United States Patent
Persoff

(10) Patent No.: US 7,213,919 B2
(45) Date of Patent: May 8, 2007

(54) METHOD AND DEVICE FOR CALIBRATING AN OPTICAL WAVEFRONT SYSTEM

(75) Inventor: Jeffrey Jonathan Persoff, San Jose, CA (US)

(73) Assignee: Visx, Incorporated, Santa Clara, CA (US)

( * ) Notice: Subject to any disclaimer, the term of this patent is extended or adjusted under 35 U.S.C. 154(b) by 304 days.

(21) Appl. No.: 10/364,973

(22) Filed: Feb. 11, 2003

(65) Prior Publication Data

US 2003/0169402 A1 Sep. 11, 2003

Related U.S. Application Data

(60) Provisional application No. 60/356,657, filed on Feb. 11, 2002.

(51) Int. Cl.
*A61B 3/00* (2006.01)
*A61B 3/10* (2006.01)

(52) U.S. Cl. ............... 351/200; 351/205; 351/246

(58) Field of Classification Search ........... 351/200, 351/205, 206, 207, 211, 212, 213–216, 221, 351/246; 356/124, 124.5; 250/201.9
See application file for complete search history.

(56) References Cited

U.S. PATENT DOCUMENTS

| | | | |
|---|---|---|---|
| 5,610,707 A * | 3/1997 | Duncan et al. ............. 356/121 |
| 6,184,974 B1 * | 2/2001 | Neal et al. ................ 356/121 |
| 6,086,204 A1 | 7/2002 | Magnante | |
| 6,460,997 B1 * | 10/2002 | Frey et al. ................. 351/211 |
| 6,485,142 B1 * | 11/2002 | Sheehy et al. ............. 351/203 |
| 6,626,535 B2 * | 9/2003 | Altmann ................... 351/177 |
| 6,637,884 B2 * | 10/2003 | Martino .................... 351/212 |
| 6,739,721 B2 * | 5/2004 | Altmann ................... 351/212 |
| 2001/0041884 A1 | 11/2001 | Frey et al. | |
| 2002/0003606 A1 | 1/2002 | Pettit | |
| 2002/0097376 A1 | 7/2002 | Applegate et al. | |
| 2003/0007127 A1 | 1/2003 | Levine | |

OTHER PUBLICATIONS

Thibos et al., "Standards for Reporting the Optical Aberrations of Eyes," V. Lakshminarayanan (Ed.) Trends in Optics and Photonics, Optical Society of America, Washington, DC, pp. 232-244.*

* cited by examiner

*Primary Examiner*—Evelyn A. Lester
(74) *Attorney, Agent, or Firm*—Townsend & Townsend & Crew LLP; Mark D. Barrish

(57) ABSTRACT

The present invention provides methods and devices for calibrating an optical wavefront system. The calibration devices of the present invention can include a body which has a proximal portion and a distal portion. A pupil can be positioned on the proximal portion of the body to aperture light. A target can be positioned on the distal portion of the body so as to reflect light back through the pupil and into the wavefront system. If the device has a lens assembly or a phase plate, the reflected light can pick up known aberrations or defocus characteristics from the lens assembly before it enters the calibration device. The known wavefront characteristic can be compared to the wavefront measurement obtained by the wavefront system to aid in calibrating the wavefront system.

15 Claims, 5 Drawing Sheets

METHOD AND DEVICE FOR CALIBRATING AN OPTICAL WAVEFRONT SYSTEM

CROSS-REFERENCES TO RELATED APPLICATIONS

The present application claims benefit to Provisional Patent Application Ser. No. 60/356,657, entitled "Method and Device for Calibrating an Optical Wavefront System," filed Feb. 11, 2002, the complete disclosure of which is incorporated herein by reference.

The present application is also related to Provisional Patent Application Ser. No. 60/356,658, entitled "Apparatus and Method for Determining Relative Positional and Rotational Offsets Between a First and Second Imaging Device" and "Provisional Patent Application Ser. No. 60/356,672, entitled "Closed Loop System and Method for Ablating Lenses with Aberrations," both filed Feb. 11, 2002, the complete disclosure of which are incorporated herein by reference.

BACKGROUND OF THE INVENTION

The present invention relates generally to a calibration device and calibration method. In particular, the present invention relates to devices and methods for calibrating an optical wavefront system that measures optical aberrations in a patient's eye.

Laser eye surgical systems typically employ a system that can track and measure the optical characteristics of the patient's eye. One promising eye measurement system uses wavefront technology that allows the surgeon to measure and treat low order and high order aberrations in and on the patient's eye. A wavefront measurement of the eye creates a high order aberration map that permits assessment of aberrations throughout the optical pathway of the eye, e.g., both internal aberrations and aberrations on the corneal surface. The aberration information can then be used to compute a custom ablation pattern so that the surgical laser system can correct the aberrations of the patient's eye.

One exemplary wavefront technology system is the VISX WaveScan™ System, which uses Hartmann-Shack wavefront sensors that can quantify aberrations throughout the entire optical system, including first and second-order sphero-cylindrical errors, coma, and third through sixth order aberrations related to coma, astigmatism, and spherical aberrations. The aberrations can be displayed to the surgeon in the form of an AcuityMap™ and/or an aberration map, for example.

However, in order to accurately map the aberrations in the patient's eye, it is required that the wavefront system be properly calibrated. If the eye measurement systems are not properly calibrated, the information derived from the wavefront will not provide the correct aberration pattern and an incorrect ablation pattern may thereafter be chosen.

Consequently, what are needed are devices and methods which can calibrate eye measurement systems, such as a wavefront system.

BRIEF SUMMARY OF THE INVENTION

The present invention provides devices and methods for calibrating an optical wavefront imaging system, such as the VISX WaveScan™ Wavefront System. It should be appreciated however, that if desired the calibration methods and devices of the present invention can be used to calibrate other eye measurement devices, such as those manufactured and/or sold by Bausch & Lomb, Wavefront Sciences, Alcon Laboratories, and the like.

In a first aspect, the present invention provides a method of calibrating an imaging device, such as a wavefront system. The method comprises directing light having known characteristics into the imaging device. The characteristics of the light are measured with the imaging device and the measured characteristics are compared with known characteristics of the light to calibrate the imaging device. If the measured phase characteristics of the reflected light do not equal the expected phase characteristics of the reflected light, the user will know that the imaging device is not calibrated correctly.

In one embodiment, the light is reflect off of a target and through an pupil or aperture assembly to aperture the light. As can be appreciated, instead of reflecting light off of a target and through the aperture assembly, it may be possible to provide a light source to generate a collimated or non-collimated light that has known characteristics.

In some embodiment, a defocus may be imparted into the reflected light, as the light will not be directed through any lenses. In other embodiments, the light can be directed through lens assemblies to change the diopter defocus and/or impart an astigmatism.

Alternatively or additionally, the light can be passed through a phase plate to impart specific, known phase characteristics to the light that is directed into the imaging device. The user can then compare the measured characteristics of the light with the expected characteristics of the light to determine if the wavefront system is properly calibrated.

In another aspect, the present invention provides a calibration tool for a wavefront system. The calibration tool comprises a body having a proximal portion and a distal portion. Target means, such as a flat or curved assembly, is positioned on the distal portion of the body for reflecting light into the wavefront system. Pupil means, such as a body having an aperture, are positioned on the proximal portion for aperturing the light beam. Optionally, attachment means may be used to couple the body to the wavefront system.

In some embodiments the calibration tool may include phase means for creating a phase profile in the reflected light and/or lens means for changing characteristics of the reflected light.

In yet another aspect, the present invention provides a calibration tool comprising a body having a proximal portion and a distal portion. A target is positioned on the distal portion of the body so as to reflect light into the image device. A pupil device is positioned on the proximal portion of the body to aperture the light, wherein at least one of the target and pupil device is movable.

In some embodiments, the calibration device includes a lens assembly that is coupled to the body to introduce at least one of focus and astigmatism into the light. Furthermore, additional high-order aberrations may also be introduced into the light by placing a phase plate with these high order aberrations approximately into the pupil. Such embodiments may or may not include a spherical or cylindrical lens.

A further understanding of the nature and advantages of the invention will become apparent by reference to the remaining portions of the specification and drawings.

DETAILED DESCRIPTION OF THE INVENTION

Figure 1A:
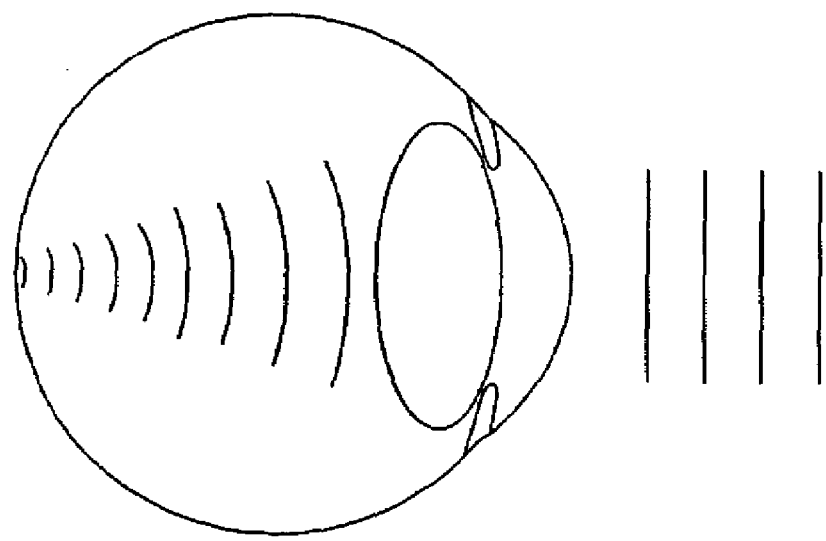
FIG. 1A illustrates light reflected off a point on the retina in which the eye has no aberrations.
Figure 1B:
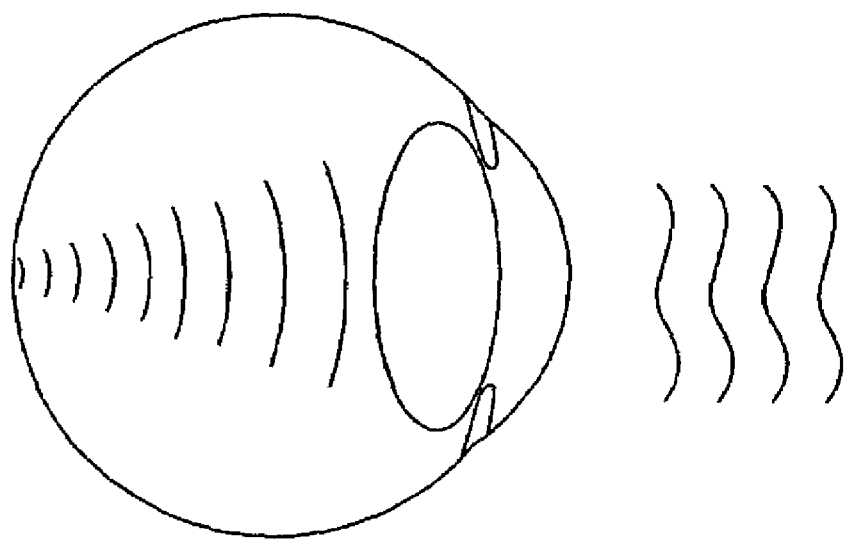
FIG. 1B illustrates light that is reflected off a point on the retina in which the eye has aberrations.

Wavefront systems collect and analyze light that is reflected off of the retina to determine the low order and high order aberrations (if any) that are present in the optical path of the patient's eye. As illustrated in FIG. 1A, light will generally focus to a point in spherical waves through an eye that has no aberrations. However, as shown in FIG. 1B, light will distort when it passes through a refractive medium that has aberrations, such as an irregular cornea or lens. Wavefront sensors, such as Hartmann-Shack sensors, are capable of measuring the distortions in the wavefront as it exits the optical tissue of the eye.

Figure 2A:
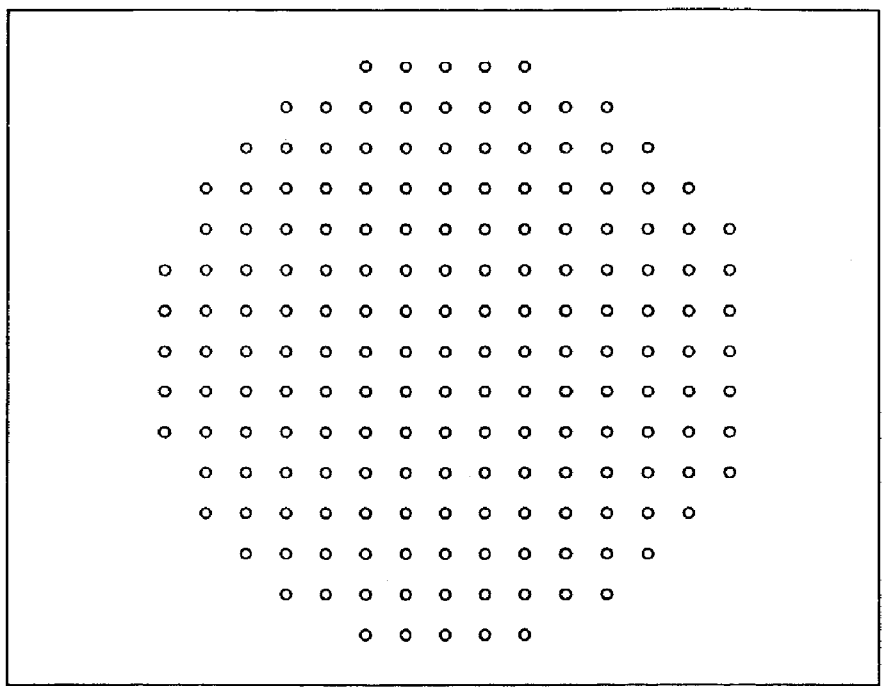
FIG. 2A is a wavefront spot pattern of the eye of FIG. 1A.

Wavefront systems can segment each wavefront using a series of sub-apertures and focus the light that travels through each sub-aperture onto an imaging device, such as a CCD, using a series of lenslets corresponding to the sub-apertures. In a flat wavefront, the focal points are in line with the optical axes of the lenslets, and, as shown in FIG. 2A, the resultant spot pattern matches the pattern of the sub-apertures (in this illustration the spot pattern is equidistant.)

Figure 2B:
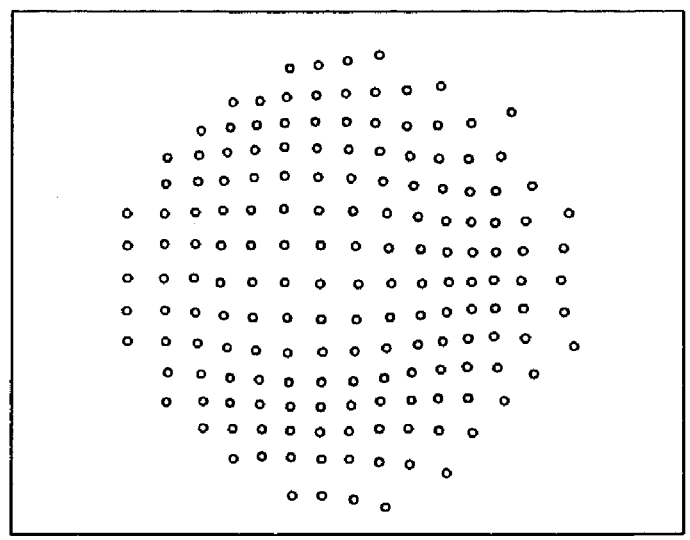
FIG. 2B is a distorted wavefront spot pattern from the eye with aberrations of FIG. 1B.

When the wavefront is distorted due to aberrations in the eye, each focal point will shift proportionate to the gradient of that part of the wave that passes through the corresponding lenslet. As shown in FIG. 2B, the resultant pattern will have an irregular form.

The wavefront data can be constructed into a color representation of visual acuity or wavefront variations over the entire area of the pupil. The map can precisely represent variations in refractive status encompassing the entire optical system, based on measurements taken of the wavefront as it exits the eye. Low order, higher-order, and spherocylindrical aberrations can be captured by wavefront systems, such as the VISX WaveScan™ System so as to allow the surgeon to make an objective assessment of the wavefront-based refraction.

The calibration methods and devices of the present invention typically use a body, such as a plurality of rods, to position an aperture and/or a phase plate relative to a target. Light is brought to a point on the target and is reflected back through the aperture and into the wavefront system being calibrated. If desired, a lens assembly can be used with the calibration device to change the diopter defocus or introduce astigmatism into the light to calibrate the wavefront system's ability to track such phase characteristics. Because the user will know the configuration and characteristics of the components of the calibration tool, the user will know the characteristics of the light (e.g., wavefront) that is delivered into the wavefront system. By comparing the expected characteristics of the wavefront with the measurements of the light from the wavefront system being tested, the user can determine if the system is properly calibrated.

Figure 3:
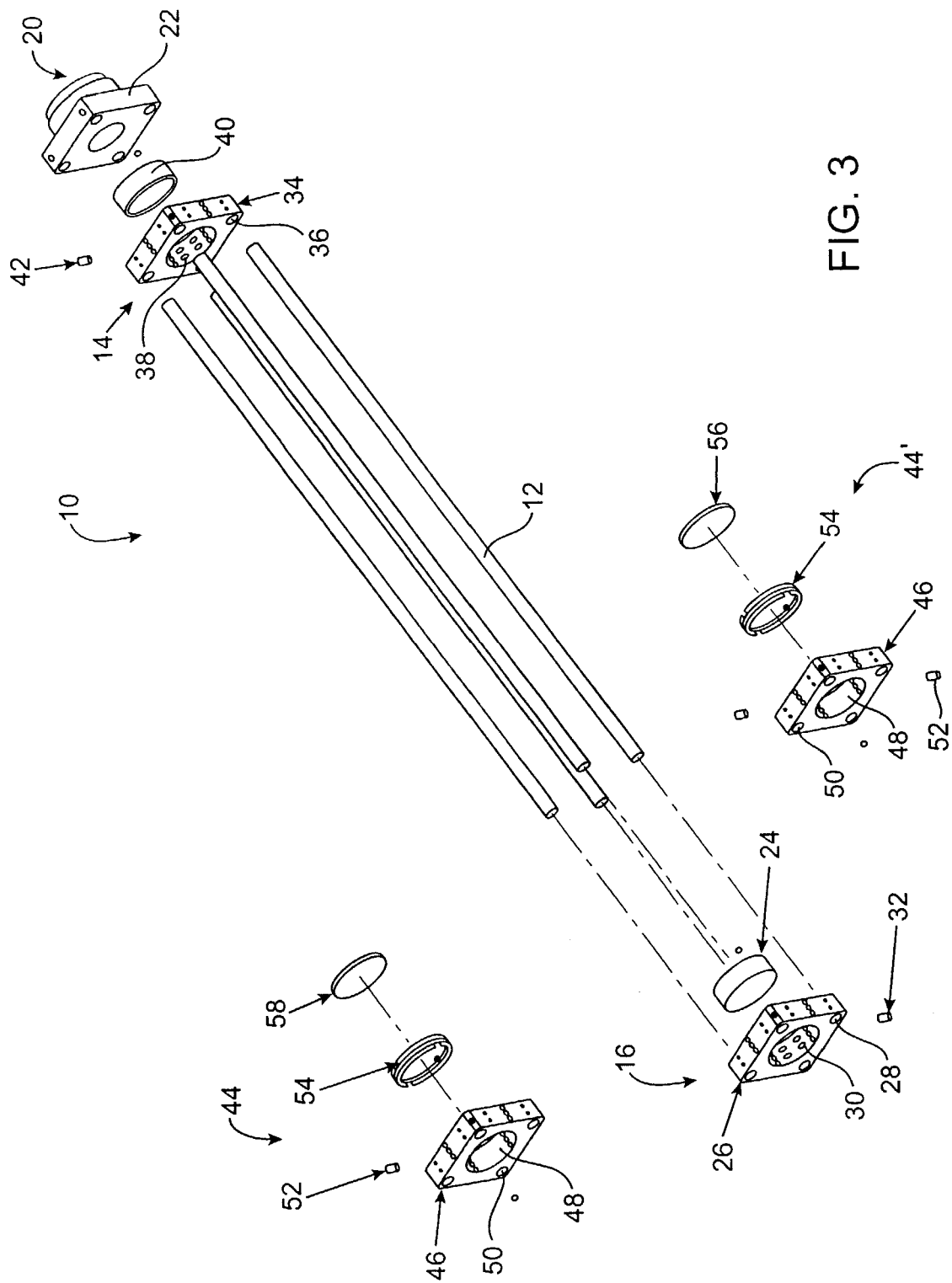
FIG. 3 is an exploded perspective view of a calibrating device of the present invention.
Figure 4:
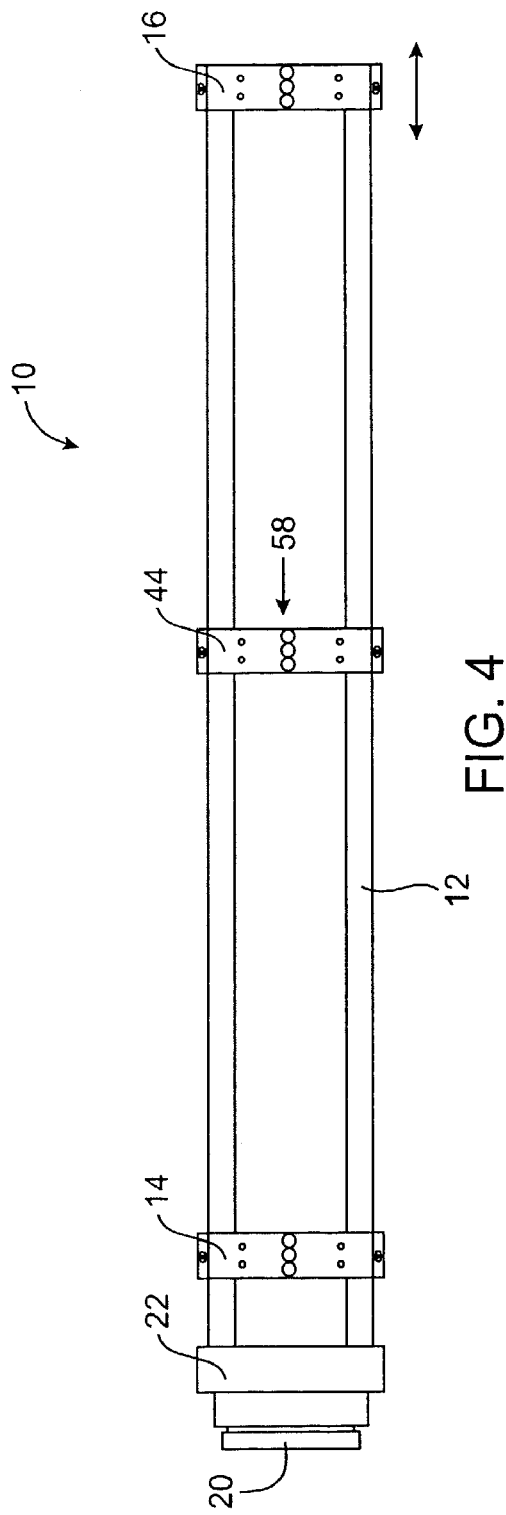
FIG. 4 is an elevational view of one exemplary embodiment of the calibrating device of the present invention having a spherical lens assembly.
Figure 5:
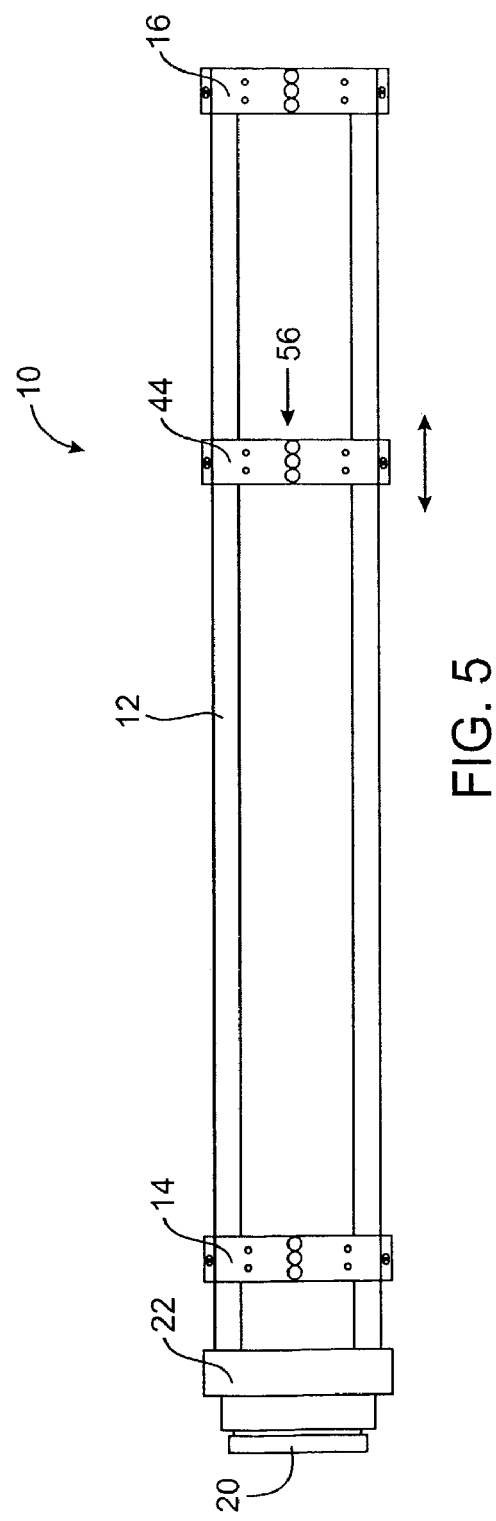
FIG. 5 is an elevational view of another exemplary embodiment of the calibrating device of the present invention having a cylindrical lens assembly.

The calibration devices and methods of the present invention can emulate the structure of the eye so as to produce an exiting wavefront pattern having certain phase characteristics, such as astigmatism or defocus, which can be analyzed by the wavefront system being calibrated. FIGS. 3 to 5 illustrate exemplary calibration devices of the present invention. In its most basic form, the calibration device 10 includes a body 12, that typically includes a plurality of elongate rods. The body can maintain a spaced position between a pupil or aperture 14 and a target 16. Light can be directed to a point on the target 16 and reflected back through the aperture 14 to the wavefront system that is being calibrated. In such a system, light that is directed to a point and reflected back through the aperture and into the wavefront system being calibrated will have aberrations as imposed by the device. Consequently, if the wavefront system is properly calibrated, its wavefront measurement should indicate wavefront variations identical (or acceptably close) to those wavefront variations imposed by the device.

Typically, for embodiments that include a spherical lens, the space between the aperture and the target will be between approximately 0.1 meters to 0.2 meters so as to calibrate between −12 diopters and +8 diopters. It should be appreciated however, that other lengths and calibration of diopters can be provided if desired.

In order to test the wavefront system's calibration of defocus and astigmatism, calibration device 10 can incorporate one or more lenses or phase plates to alter the characteristics of the wavefront that exits the calibration device so that the light reflected through the aperture will have certain phase characteristics, including at least some defocus, aberrations, astigmatism, and the like. The actual wavefront measurement from the wavefront system can be compared with the expected wavefront measurement to help calibrate the device under test.

In exemplary embodiments, to attach the calibration device to the wavefront system, calibration device 10 can include an attachment means 20 such as threads, clips, or the like, to position the calibration device within the optical path of the system being calibrated. In the illustrated embodiment, threads 20 can screw into a corresponding threaded opening in an optical head of the wavefront system (not shown). Threads 20 can be coupled to an adaptor 22 that is rigidly attached to body 12 so as to accurately position aperture 14 and target 16 in an optical path of the wavefront system. It should be appreciated, however, that in other embodiments, the calibration device need not have an attachment means 20, and can merely be placed on a calibration rail (not shown), or the like, to position the calibration device in the optical path of the system being calibrated As shown most clearly in FIG. 3, target 16 can be either a flat or curved assembly that can receive light to a point and reflect the light back to the wavefront system that is being calibrated. In exemplary embodiments, target 16 is comprised of a disk 24 composed of a material that can reflect light, such as an aluminum, or other material having a reflective surface, such as a flat white layer. In one configuration, the target 16 may have matte white surface so as to reduce the amount of unwanted light reflections. For example, target 16 may comprise Spectralon®, which may reflect optically diffuse light back to the imaging device.

Target 16 can be attached to body 12 through a housing 26. Housing 26 typically has a plurality of openings 28 for receiving rods 12 and a central aperture 30 for housing the target disk 24. Target can be fixed in position on the rods through use of attachment means 32, such as screws, clips, or the like. In embodiments where the diopters are to be adjusted or a defocus is desired to be imparted into the wavefront, target 16 will be movable. Loosening of the attachment means allows target 16 to be moved along a longitudinal axis of rods 12 so as to change the diopters and to impart a defocus into the exiting wavefront. In embodiments in which a cylindrical lens is used, the target will be held stationary and the cylindrical lens will be movable.

Typically, calibration device 10 can be used to calibrate between −12 diopters and +8 diopters. It should be appreciated however, that a larger range of diopters can be measured by changing the different optical powers and configuration of the components of calibration device 10.

Referring again to FIG. 3, pupil or aperture 14 can be coupled to body 12 through a housing 34 that has a plurality of openings 36 for receiving rods 12. A central aperture 38 can receive an element 40 that includes the pupil and/or a phase plate, as will be described below. Typically, housing 34 can removably receive screws 42, or other attachment means, for attaching housing 34 to rods 12.

The present invention can take a variety of forms. In a first embodiment, the present invention is as described above, in which calibration device includes a target 16 and an aperture 14. In a second embodiment, a phase plate 40 can be added to the aperture 38 so as to create a phase profile in a pupil plane for the light exiting the calibration tool. In one specific configuration, the calibration device includes both a phase plate and an aperture 40, collectively.

In a third embodiment, calibration device 10 can include a lens assembly 44 which can change the characteristics of the light passing through the calibration device 10 such that specific aberration characteristics can be imparted into the exiting wavefront that is to be measured by the wavefront system under test. The result of the measurement can then be compared to the results expected from the configuration of the calibration device 10 in order to calibrate the wavefront device under test.

Lens assembly 44 can be positioned between target 16 and aperture 14. Depending on the type of lens, the lens assembly 44 can be used to impart an astigmatism or defocus into the wavefront that exits the calibration device 10. Similar to the target, lens assembly can include a housing 46 that has a central aperture 48 and a plurality of openings 50 for receiving rods 12. Attachment means 52 can be used to release and secure the position of the housing 46 relative to the rods. A mounting device 54 can attach a lens, such as a negative or positive spherical or cylindrical lens, to the assembly 44. FIG. 3 shows both a cylindrical lens 56 and a spherical lens 58 that can be used with the calibration device.

As shown in FIG. 4, in embodiments where it is desired to impart a defocus into the exiting wavefront, a spherical lens 58 can be used. In such embodiments the relative positions of the lens assembly 44 and the aperture 14 can be maintained, while the target 16 will be movable relative to the lens assembly 44.

As shown in FIG. 5, in embodiments where it is desired to impart an astigmatism into the exiting wavefront, a cylindrical lens 56 can be used. In such embodiments, as shown by the arrow, the lens assembly 44 can be movable along the longitudinal axis of the body 12 and rotatable about the longitudinal axis so as to change the amount and axis of astigmatism. The relative position of the aperture 14 and target 16 will generally be maintained, while the position of the lens assembly 44 can be moved.

In a fourth embodiment, the calibration device of the present invention can include a phase plate 40 and a lens assembly 44 that includes a cylindrical lens or a spherical lens assembly.

In a fifth embodiment, the calibration device of the present invention can include a phase plate 40, without a lens assembly.

In any of the embodiments described above, mounting device 54 may be used to tilt the lens assembly 44 and/or phase plate 40 to a non-orthogonal angle relative to the optical axis of the imaging device so as to direct undesired specular light reflections from the lens or phase plate away from the optical entrance aperture of the imaging device under test.

Figure 6:
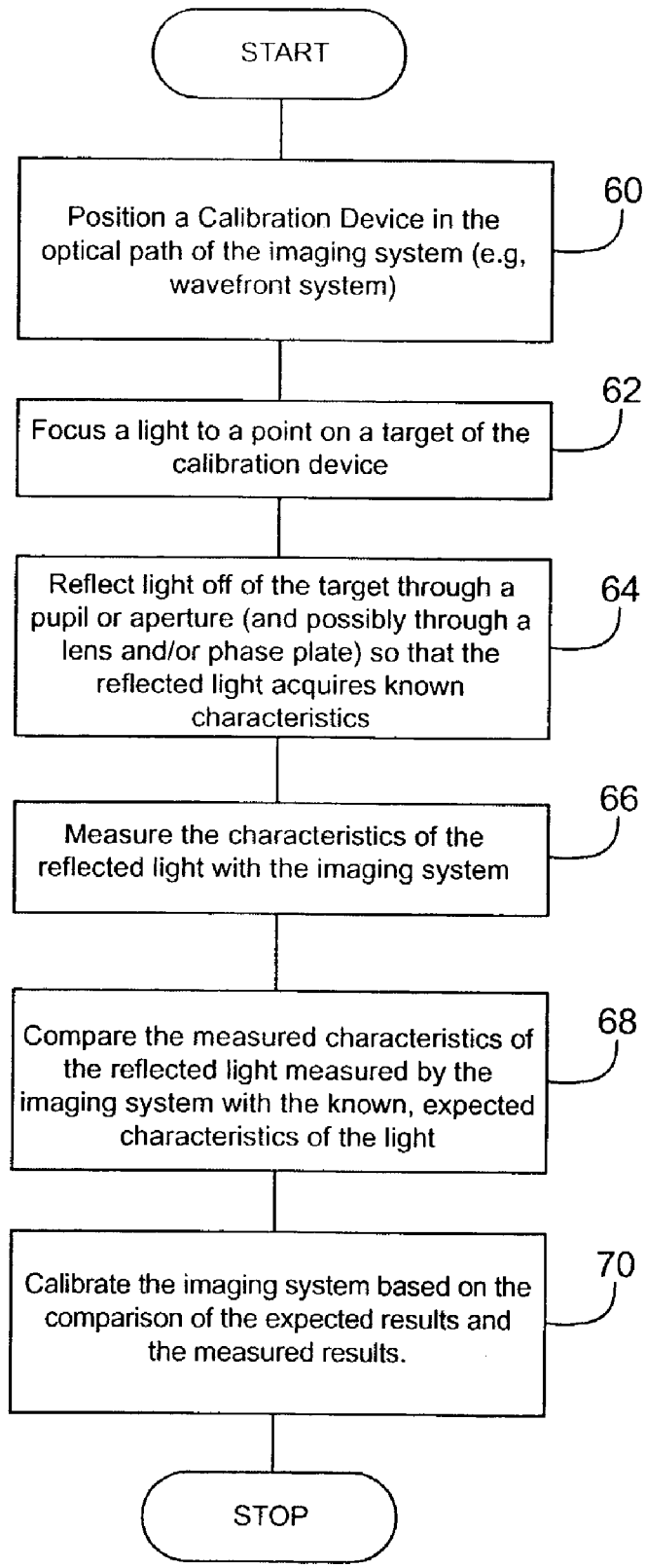
FIG. 6 schematically illustrates a method of the present invention.

As illustrated schematically in FIG. 6, in use, the calibration device of the present invention is positioned in the optical path of the wavefront system (or other imaging system) that is being calibrated (Step 60). A light is focused to a point on a target of the calibration device (Step 62) and the light is reflected off of the target and through a pupil or aperture back into the wavefront system (Step 64). If no lens assembly or phase plate is used, the light reflected back into the wavefront system will have only a defocus and if the wavefront system is calibrated correctly, the wavefront system would measure the wavefront having the expected defocus. If the user desires to calibrate the system's ability to measure astigmatism, a different positive or negative defocus, and/or other high order or low order aberrations, the user can position a lens assembly and/or a phase plate in the optical path of the reflected light so as to impart such desired characteristics into the exiting wavefront.

The characteristics of the light are measured with the wavefront system (Step 66) and the measured characteristics of the light are compared with the expected characteristics of the light that exited the calibration device (Step 68). The wavefront system can thereafter be calibrated based on the comparison of the expected measurements and the actual measurements (Step 70). If the measured characteristics of the light are the same as the known characteristics of the light, then no additional calibration of the wavefront system is necessary.

While the above is a complete description of the preferred embodiments of the inventions, various alternatives, modifications, and equivalents may be used. For example, if desired, body 12 can include distance markings to inform the user of the relative distance between the lens, aperture, and/or target. Although the foregoing has been described in detail for purposes of clarity of understanding, it will be obvious that certain modifications may be practiced within the scope of the appended claims.

What is claimed is:

1. A method of calibrating an ocular wavefront system for eye wavefront measurements, the wavefront system transmitting a wavefront-generating light, the method comprising:

reflecting the wavefront-generating light off a target of a calibration device;

directing the reflected light from the target through an aperture assembly of the calibration device and into the wavefront system without transmitting the light through any lens of the calibration device and without transmitting the light through any phaseplate of the calibration device, the directed light comprising known diopter defocus wavefront variations induced by a position of the target, wherein directing the light through the aperture assembly apertures the reflected light;

measuring a wavefront of the light directed into the wavefront system, the aperture and target emulating eye structures; and comparing the measured wavefront of the light with the known wavefront variations of the light to determine if the wavefront system is properly calibrated.

2. The method of claim 1 comprising modifying a distance between the target and the aperture assembly to calibrate diopters.

3. The method of claim 1 wherein the wavefront system comprises a Hartmann-Shack sensor assembly.

4. The method of claim 1 further comprising adjusting the wavefront system based on the comparison of the measured characteristics and the known characteristics of the light.

5. The method of claim 1 wherein the target comprises a flat surface.

6. The method of claim 1 wherein the target compnses a curved shape.

7. A wavefront system calibration tool, the wavefront system transmitting a wavefront-generating light suitable for eye wavefront measurements, the calibration tool comprising:

a body comprising a proximal portion and a distal portion;

a target positioned on the distal portion of the body that reflects the wavefront-generating light from the wavefront system back into the wavefront system; and a pupil device positioned on the proximal portion of the body to aperture the reflected light such that the aperture and target emulate eye structures in the eye wavefront measurements, wherein the light transmitted through the pupil device and to the wavefront system has an exiting wavefront with wavefront distortions, the wavefront distortions consisting of target position induced diopter defocus.

8. The calibration tool of claim 7 wherein the target is movably coupled to the body.

9. The calibration tool of claim 7 wherein the body comprises a plurality of spaced rods.

10. The calibration tool of claim 7 wherein the wavefront comprises known aberration characteristics.

11. The calibration tool of claim 7 wherein the calibration tool does not include a lens.

12. A calibration tool for a wavefront system suitable for eye wavefront measurements, the calibration tool comprising:

a body comprising a proximal portion and a distal portion;

target means positioned on the distal portion of the body for reflecting light from the wavefront system back into the wavefront system;

pupil means positioned on the proximal portion for aperturing the light and emulating a pupil of an eye; and wavefront altering means for imposing a known wavefront characteristic on the reflected light without transmitting the light from a phase plate or lens.

13. The calibration tool of claim 12 further comprising attachment means for coupling the body to the wavefront system.

14. The calibration tool of claim 13 wherein the attachment means comprises at least one of clips, clamps, screws or adhesive.

15. A method of calibrating a wavefront system using a calibration device, the method comprising:

optically coupling the calibration device with the wavefront system;

directing light rays comprising known wavefront variations from a target of the calibration device without directing the light through any lens of the calibration device and without directing the light through any phase plate of the calibration device;

measuring the wavefront variations of the light directed from the target;

determining wavefront system correction factors for the wavefront system from differences between the measured wavefront variations and the known wavefront variations, and optically decoupling the calibration device from the wavefront system and optically coupling the wavefront system with an eye so as to measure a wavefront of the eye.

* * * * *